United States Patent [19]

Anderson et al.

[11] Patent Number: 4,590,431

[45] Date of Patent: May 20, 1986

[54] INDUCTION VOIDMETER

[75] Inventors: Thomas T. Anderson, Downers Grove; Conard J. Roop, Lockport; Kenneth J. Schmidt, Midlothian; John Brewer, Oak Lawn, all of Ill.

[73] Assignee: The United States of America as represented by the Department of Energy, Washington, D.C.

[21] Appl. No.: 564,129

[22] Filed: Dec. 21, 1983

[51] Int. Cl.[4] .......................................... G01N 27/02
[52] U.S. Cl. .................................. 324/443; 324/445; 324/239
[58] Field of Search ................... 324/DIG. 1, 62, 439, 324/442, 443, 445, 204, 236–239, 241; 73/861.41, 19; 376/250, 256

[56] References Cited

U.S. PATENT DOCUMENTS

| | | | |
|---|---|---|---|
| 2,435,043 | 1/1948 | Lehde | 73/194 |
| 3,234,458 | 2/1966 | Bean et al. | 324/239 |
| 3,735,252 | 5/1973 | Azuma | 324/DIG. 1 |
| 3,748,576 | 7/1973 | Sigournay | 73/861.41 |
| 4,144,741 | 3/1979 | Nakamoto | 73/19 |

OTHER PUBLICATIONS

G. Thatcher, "Electromagnetic Flowmeters for Liquid Metals", Modern Developments in Flow Measurement, Peregrinus, pp. 359–380, 1971.

F. Harris, Electrical Measurements, John Wiley & Sons, 1965, pp. 724, 725.
Standard Handbook for Mechanical Engineers, 7 Edition, T. Baumeister, Editor, 1967, pp. 5-77 to 5-81, 16-10.
D. E. Wiegand, The Eddy Current Flowmeter, ANL Report, No. 7554, Aug. 1969.
Anderson et al, Acoustics and Voiding Dynamics during SLSF Simulations of LMFBR Undercooling Transients, Fluid Transients and Acoustics in the Power Industry, ASME, NY, 1978, pp. 231–240.
GenRad Catalog, pp. 6–7, 1983, on Impedance Bridges.

Primary Examiner—Michael J. Tokar
Attorney, Agent, or Firm—Jeannette M. Walder; Walter L. Rees; Judson R. Hightower

[57] ABSTRACT

An induction voidmeter for detecting voids in a conductive fluid may comprise: a four arm bridge circuit having two adjustable circuit elements connected as opposite arms of said bridge circuit, an input branch, and an output branch; two induction coils, bifilarly wound together, connected as the remaining two opposing arms of said bridge circuit and positioned such that the conductive fluid passes through said coils; applying an AC excitation signal to said input branch; and detecting the output signal generated in response to said excitation signal across said output branch. The induction coils may be located outside or inside a non-magnetic pipe containing the conductive fluid.

12 Claims, 5 Drawing Figures

INDUCTION VOIDMETER

CONTRACTUAL ORIGIN OF THE INVENTION

The U.S. Government has rights in this invention pursuant to Contract No. W-31-109-ENG-38 between the U.S. Department of Energy and The University of Chicago representing Argonne National Laboratory.

BACKGROUND OF THE INVENTION

This invention relates generally to an apparatus for detecting voids in a conductive fluid. The present invention was developed specifically to detect voids in liquid sodium in conjunction with safety tests as part of the national Liquid Metal Fast Breeder Reactor safety development program, but is applicable to detect voids in any conductive fluid. Although there are numerous void detection devices available, various contraints of the sodium loop required a fresh approach. For example, the extremely limited space available eliminated most existing devices including ultrasonics. The pulsed-radiation environment eliminated gramma-ray and neutron attenuation methods. Internal probes could not be used because of the limited access to the sodium volume. And, the heavy-wall pipe would shunt electrical currents injected into the sodium via the electrical conductivity method.

The principle of operation of the present invention is based on inducing eddy currents in a conductive fluid by an external alternating-current magnetic field. Eddy currents, or more precisely, magnetic flux coupling, is the principle behind the eddy current flowmeter which is used to measure velocity of a conductive fluid. However, since an effective void detector must be insensitive to flow rate, the present invention bears little resemblance to a flowmeter.

Therefore, it is an object of the present invention to provide a void detector that can be used within the space limitations of a sodium loop.

It is another object of the present invention to provide a void detector that is insensitive to flow rates of the conductive fluid.

It is yet another object of the present invention to provide a void detector that can be used in a pulsed-radiation environment.

Additional objects, advantages and novel features of the invention will be set forth in part in the description which follows, and in part will become apparent to those skilled in the art upon examination of the following or may be learned by practice of the invention.

SUMMARY OF THE INVENTION

To achieve the foregoing and other objects and in accordance with the purpose of the present invention, an apparatus for detecting voids in a conductive fluid may comprise: a four arm bridge circuit having two adjustable circuit elements connected as opposite arms of said bridge circuit, an input branch, and an output branch; two induction coils, bifilarly wound together, connected as the remaining two opposing arms of said bridge circuit and positioned such that the conductive fluid passes through said coils; means for applying an AC excitation signal to said input branch; and means for detecting the output signal generated in response to said excitation signal across said output branch. The induction coils may be located outside or inside a non-magnetic pipe containing the conductive fluid.

When the excitation signal is applied to the induction coils, the magnetic fields generated excite eddy currents in the conductive fluid, which affect the inductance of the bridge circuit. The adjustable circuit elements are then adjusted so that a balance condition occurs across the output branch. When a void occurs in the conductive fluid, there is a change in the electromagnetic coupling between the induction coils and the conductive fluid, which behaves essentially as a oneturn shorted coil. Since the induction coils are connected as opposing bridge arms, the resulting changes in impedance in these two coils causes one output terminal to unbalance in one direction and the other output terminal to unbalance in the opposite direction. Since there are two coils, the change in the self-inductance for two coils is twice that for one. In addition to the self-inductance of each coil is added the mutual inductance between the two coils. For the close to unity coupling factor observed, total inductance (mutual plus self) per coil is double the self-inductance. Hence, the output signal produced by the present invention is four times the signal of a single induction coil.

DESCRIPTION OF THE DRAWINGS

The present invention is illustrated in the accompanying drawings wherein.

DETAILED DESCRIPTION OF A PREFERRED EMBODIMENT

Figure 1:
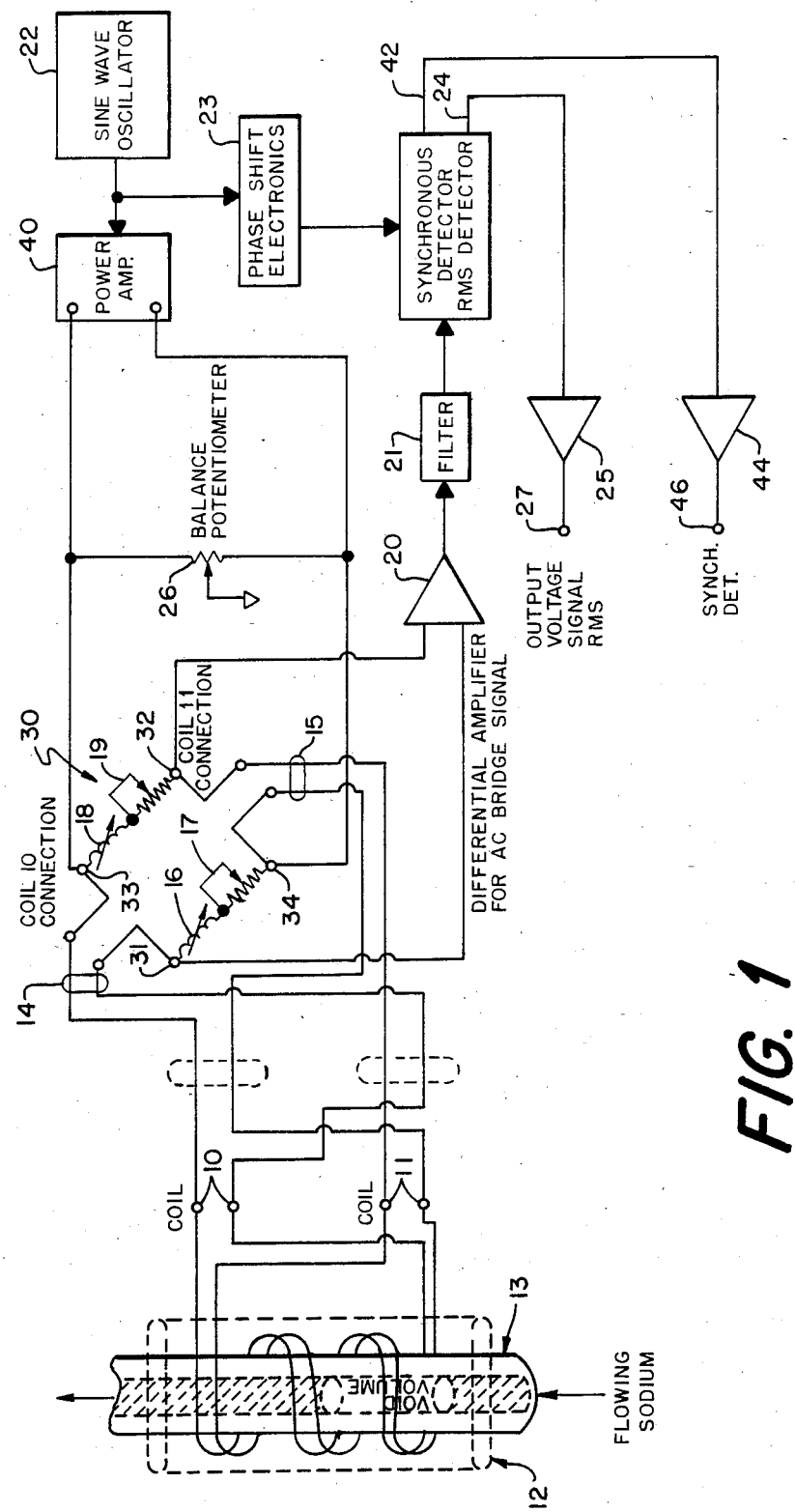
FIG. 1 is an electrical block diagram of the induction voidmeter.

Referring to FIG. 1, bifilar-wound wire is separated into two induction coils 10 and 11. Coils 10 and 11 are wound around containment pipe 13 which is shielded by a ferromagnetic shield (not shown). The effect of the magnetic shielding is to constrain magnetic field 12 axially as it penetrates into the pipe volume, providing a local measure of void immediately under the coil. Coils 10 and 11 are bifilar-wound to match electrical impedances and to eliminate changes in impedance due to temperature changes. Coils 10 and 11 are connected as opposite arms of bridge circuit 30 via connections 14 and 15 respectively. Bridge circuit 30 has two adjustable arms: one arm consisting of adjustable inductor 16 and adjustable resistor 17, the other consisting of adjustable inductor 18 and adjustable resistor 19. Sine-wave oscillator 22 provides an excitation signal amplified by power amplifier 40 through balance potentiometer 26 to the bridge input across terminals 33 and 34. The bridge output signal, across terminals 31 and 32, is amplified by amplifier 20, filtered by band pass filter 21, then applied to RMS detector 24 and synchronous detector 42. The output of RMS detector 24 is amplified by amplifier 25 where it may be read at terminal 27. Synchronous detector 42 compares the output 10 the excitation signal from oscillator 22 through phase-shift electronics. The output of synchronous detector 42 is amplified by amplifier 44 where it may be read at terminal 46. The excitation and output signals are balanced with respect to electrical ground to minimize parasitic cable currents during reactor power burst.

Figure 2A:
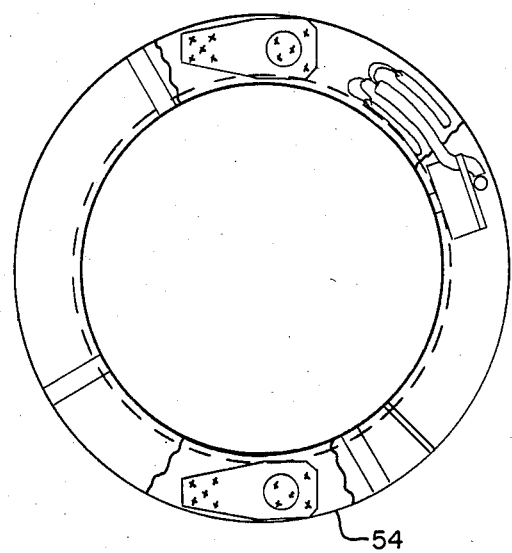
FIG. 2A-2C show details of construction of a voidmeter constructed to be mounted outside a pipe.
Figure 2B:
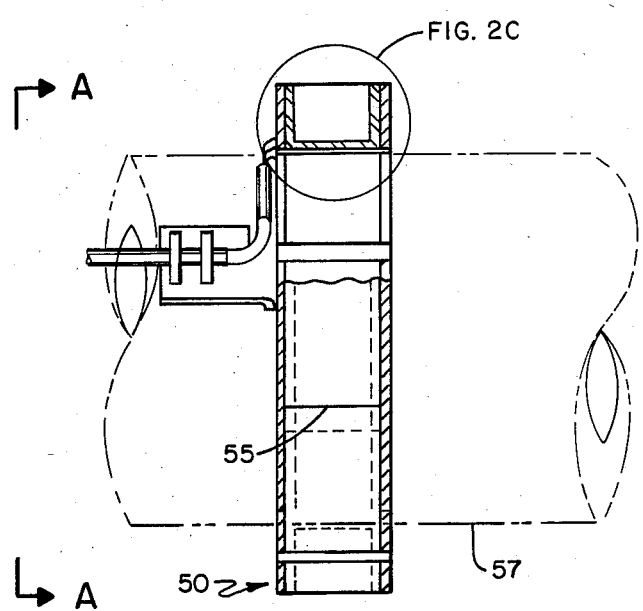
Figure 2C:
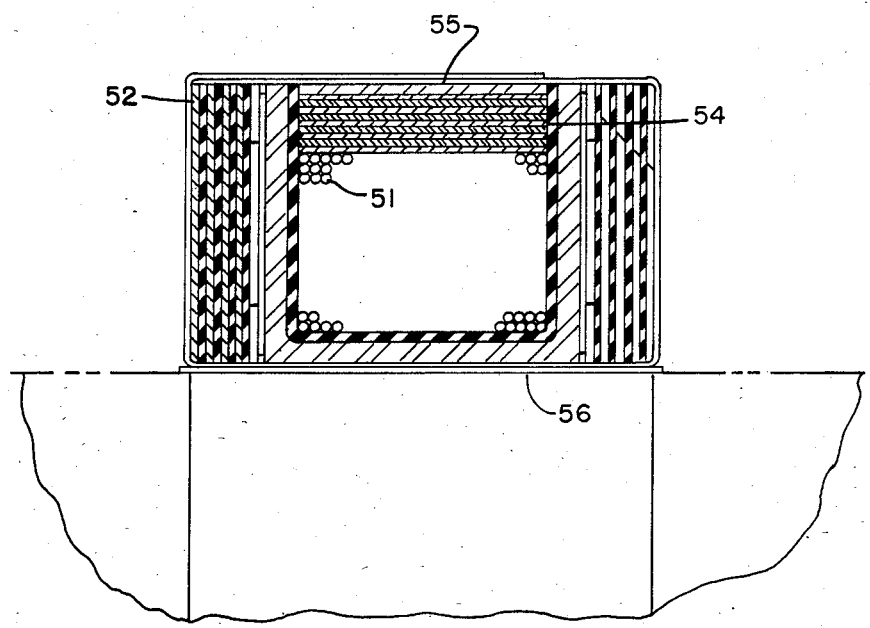

In FIGS. 2A-2C, an induction voidmeter 50 for use on a pipe containing liquid sodium is shown. In FIG. 2A voidmeter 50 is mounted on pipe 57; four conductor shielded cable 53 connects the voidmeter to the electronics circuitry (not shown). Voidmeter 50 is formed by winding high temperature ceramic insulated magnet wire 51 about stainless steel spool 54. Zirconia cloth is wrapped about the wire, which is held in place by band 55. Magnetic shielding 52 surrounds the coil and constrains the magnetic field axially. Spool 54 is mounted on pipe 57, which is also covered with zirconia cloth 56. The zirconia cloth provides radial tolerance and thermal insulation.

The magnet wire material may be 14 mil copper clad with 10% nickel by weight. The nickel is required to prevent oxidation of the copper and to provide a base for adherence of the high-temperature ceramic insulation. The magnet wire is bifilar-wound to form two coils of 200 turns each.

The excitation signal may have a frequency between 200 Hz and 600 Hz. At 430 Hz the phase-shift electronics permitted a response time of 15 milliseconds. The induction voidmeter is extremely compact ($\frac{1}{2}$ inch to 1 inch). When the sodium voids, coil impedance changes about 1% to generate a useable bridge-output signal of 50 millivolts, independent of sodium flowrate.

EXAMPLE

Figure 3:
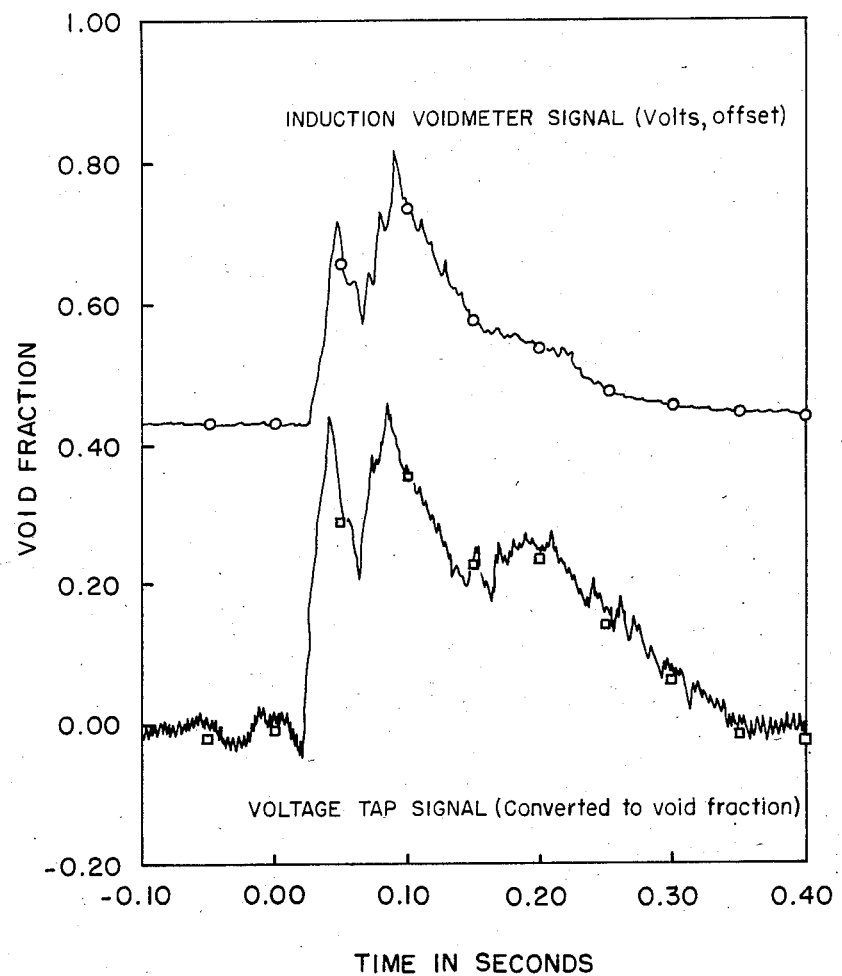
FIG. 3 shows the results of a void test using the voidmeter in comparison to a voltage tap on a thin-walled pipe.

Two induction voidmeters have been used successfully to measure gas injection and urania dispersion within the CAMEL loop during an out of pile test. The voidmeter detected the upward-moving sodium interface while the loop was being filled with sodium and later the voidmeter was compared with voltage taps on the pipe wall (thin pipe). In FIG. 3 the output signal (27) of the voidmeter (converted to void fraction) is compared to the output signal of a voltage tap (on a thin wall pipe). The voidmeter signals matched almost exactly those of the voltage tap of upward using vapor bubbles when molten fuel was injected into the sodium coolant. It should be noted that in a full scale reactor loop, the pipe walls are not thin enough to permit use of a voltage tap.

The embodiments of this invention in which an exclusive property or privilege is claimed are defined as follows:

1. Apparatus for detecting voids in a conductive fluid comprising:
    a four arm bridge circuit having two adjustable circuit element connected as opposing arms of said bridge circuit, an input branch, and an output branch;
    two induction coils, bifilarly wound together, connected as the remaining two opposing arms of said bridge circuit, and positioned such that the conductive fluid passes through said coils;
    means for applying an AC excitation signal to said input branch; and
    means for detecting the output signal generated in response to said excitation signal across said output branch.

2. The apparatus of claim 1 wherein said induction coils are wound around a pipe containing the conductive fluid.

3. The apparatus of claim 1 wherein said induction coils are mounted inside a pipe containing the conductive fluid.

4. The apparatus of claim 2 wherein the conductive fluid is sodium.

5. The apparatus of claim 4 wherein said induction coils comprise 200 turns each of insulated copper wire clad with nickel.

6. The apparatus of claim 2 further comprising magnetic shielding surrounding said induction coils.

7. The apparatus of claim 1 wherein each of said adjustable circuit means comprises a variable inductor in series with a variable resistor.

8. The apparatus of claim 1 wherein said detection means comprises an RMS detector.

9. The apparatus of claim 1 wherein said detection means comprises a phase-synchronous detector.

10. The apparatus of claim 1 wherein said excitation signal has a frequency in the range of 200 Hz to 600 Hz.

11. The apparatus of claim 1 wherein said excitation frequency is 430 Hz.

12. A method of detecting voids in a conductive fluid comprising the steps of:
    (a) applying an AC excitation signal to two induction coils, bifilarly wound together, connected as opposing arms of a four arm bridge circuit and positioned such that the conductive fluid passes through said coils;
    (b) adjusting the two adjustable circuit elements of said bridge circuit, connected as the remaining two opposing arms of said bridge circuit, until a balance condition occurs across the output branch of said bridge circuit; and
    (c) detecting the unbalance across the output branch as a result of a void occuring in the conductive fluid causing a change in impedance in the induction coils.

* * * * *